US012697423B2

(12) United States Patent (10) Patent No.: US 12,697,423 B2
Arnold et al. (45) Date of Patent: Aug. 4, 2026

(54) UREA MONITORING DURING DIALYSIS FOR IMPROVED QUALITY CONTROL AND TREATMENT GUIDANCE

(71) Applicant: University of Iowa Research Foundation, Iowa City, IA (US)

(72) Inventors: Mark Arnold, Iowa City, IA (US); Jonathon Olesberg, Sandia Park, NM (US)

(73) Assignee: University of Iowa Research Foundation, Iowa City, IA (US)

( * ) Notice: Subject to any disclaimer, the term of this patent is extended or adjusted under 35 U.S.C. 154(b) by 396 days.

(21) Appl. No.: 18/030,339

(22) PCT Filed: Oct. 5, 2021

(86) PCT No.: PCT/US2021/053598
§ 371 (c)(1),
(2) Date: Apr. 5, 2023

(87) PCT Pub. No.: WO2022/076432
PCT Pub. Date: Apr. 12, 2022

(65) Prior Publication Data
US 2023/0381384 A1 Nov. 30, 2023

Related U.S. Application Data

(60) Provisional application No. 63/087,600, filed on Oct. 5, 2020.

(51) Int. Cl.
*A61M 1/16* (2006.01)
*A61M 1/34* (2006.01)
(Continued)

(52) U.S. Cl.
CPC ........ *A61M 1/1609* (2014.02); *A61M 1/1607* (2014.02); *A61M 1/3417* (2014.02);
(Continued)

(58) Field of Classification Search
CPC .............. A61M 1/1609; A61M 1/1607; A61M 1/3417; A61M 2202/0498;
(Continued)

(56) References Cited

U.S. PATENT DOCUMENTS 5,308,315 A 5/1994 Khuri et al.
6,126,831 A 10/2000 Goldau et al.
(Continued)

OTHER PUBLICATIONS

Canaud et al., Urea as a marker of adequacy in hemodialysis: Lesson from in vivo urea dynamics monitoring, Kidney International, vol. 58, Supplement 76, pp. S28-S40 (Year: 2000).*
Abe, Takayuki , et al., "In vitro Evaluation of Solute Removal Characteristics in Intermittent Infusion Hemodiafiltration", Blood Purification, vol. 48, Dec. 1, 2019, 11-16.
(Continued)

*Primary Examiner* — Rebecca E Eisenberg
*Assistant Examiner* — Brandon W. Levy
(74) *Attorney, Agent, or Firm* — Dentons Davis Brown; Matthew Warner-Blankenship; Joseph Schneiders

(57) ABSTRACT

A method of measuring a dialysis efficacy, dialysis dose, and impacts of dialysis on a patient. The method including measuring a concentration of urea in a dialysis effluent over time; determining a rate of change in urea concentration; and determining the rate of peripheral perfusion from the rate of change in urea concentration. The concentration of urea may be taken in real time or near-real time. The method including determining changes in the rate of peripheral perfusion in real time or near real-time. The method including detecting disequilibrium between the core and peripheral blood and early onset of clinically adverse conditions.

17 Claims, 7 Drawing Sheets

(51) Int. Cl.
G16H 10/40 (2018.01)
G16H 40/67 (2018.01)

(52) U.S. Cl.
CPC ............. G16H 10/40 (2018.01); G16H 40/67 (2018.01); *A61M 2202/0498* (2013.01); *A61M 2205/3313* (2013.01); *A61M 2205/3317* (2013.01)

(58) Field of Classification Search
CPC .. A61M 2205/3313; A61M 2205/3317; A61M 1/1613; A61M 1/361; A61M 2205/3306; A61M 1/1605–1615; A61M 1/3609–3612; G16H 10/40; G16H 40/67; A61B 5/14546; A61B 5/6866
See application file for complete search history.

(56) References Cited

U.S. PATENT DOCUMENTS

| | | | |
|---|---|---|---|
| 6,258,027 B1 * | 7/2001 | Sternby | ................. A61M 1/165 600/366 |
| 8,204,565 B2 | 6/2012 | Arnold et al. | |
| 2008/0086273 A1 | 4/2008 | Schults et al. | |
| 2019/0125951 A1 | 5/2019 | Anand et al. | |

OTHER PUBLICATIONS

De Miranda, Ana Carolina , et al., "Monitoring peripheral perfusion in sepsis associated acute kidney injury: Analysis of mortality", PLOS One, vol. 15, Issue 10, Oct. 14, 2020, 1-14.
Gotch, Frank A., et al., "A mechanistic analysis of the National Cooperative Dialysis Study (NCDS)", Kidney International, vol. 28, Sep. 1, 1985, 526-534.

* cited by examiner

Urea concentration can
be measured in blood or
effluent dialysate stream

UREA MONITORING DURING DIALYSIS FOR IMPROVED QUALITY CONTROL AND TREATMENT GUIDANCE

CROSS-REFERENCE TO RELATED APPLICATION(S)

This application claims the benefit under 35 U.S.C. § 119(e) to U.S. Provisional Application 63/087,600, filed Oct. 5, 2020, and entitled "Urea Monitoring During Dialysis for Improve Quality Control and Treatment Guidance," which is hereby incorporated herein by reference in its entirety for all purposes.

GOVERNMENT SUPPORT

This invention was made with government support under Grant No. DK002925 awarded by the National Institutes of Health. The government has certain rights in the invention.

TECHNICAL FIELD

The disclosure relates to dialysis and devices, systems, and methods for analysis and monitoring the efficacy of dialysis during treatment.

BACKGROUND

There are various known approaches for evaluating the efficacy of dialysis. For example, certain known dialysis machines include a form of dose monitoring known as ionic dialysance. Ionic dialysance is a method for periodically measuring the rate of transport of ions across the dialysis membrane. This provides a measure of the membrane clearance (K), one of the parameters in an expression for dialysis dose expressed as: Kt/V (where V is a measure of volume of distribution of urea, approximately equal to patient's total body water and t is time). It is understood that ionic dialysance may be useful in that it provides a periodic measurement of whether the membrane is functioning as expected. The delivered dialysis dose can be estimated from the ionic dialysance result if t and V are known and the patient's perfusion is normal. But, perfusion is often variable and, as such, the actual delivered dose may be different from that which is calculated from the ionic dialysance.

In another example, the effectiveness of dialysis (the delivered dose) is estimated from a measurement of urea in blood samples taken before and after a dialysis treatment. Conducting this measurement requires additional treatment time and expense and, as such, is only conducted periodically, such as once or twice a month (i.e., one out of every 7 or 14 treatments a patient receives).

It is understood that it takes 30 minutes or more for the concentration of urea in the patient to equilibrate. To avoid requiring the patient to wait an extra 30 minutes after the end of their treatment, the post-dialysis blood draw is taken immediately after cessation of dialysis and standard approximations are made to estimate the equilibrated blood urea concentration from this non-equilibrium sample.

The precise timing of this final blood draw is a source of error in the resulting estimate of delivered dialysis dose. In addition, the formulas used to estimate the equilibrated blood urea concentration depend on assumptions about the rate of perfusion during the treatment and provide no information about whether those assumptions are correct for the particular dialysis treatment.

There is a need in the art for improved methods of monitoring, analyzing, and evaluating dialysis treatments, including real-time or near real-time measurement of perfusion rate.

BRIEF SUMMARY

The disclosure relates generally to devices, systems, and methods that may be used to improve and optimize dialysis treatment. Implementations disclosed herein allow for real-time or near real-time monitoring of peripheral perfusion in dialysis patients. This measurement of peripheral perfusion is an important factor in analyzing the effectiveness of a dialysis treatment, detecting, and mitigating adverse hemodynamic events, and preventing adverse clinical outcomes.

In Example 1, a method of measuring efficacy and impacts of dialysis comprising measuring a concentration of urea in a dialysis effluent over time, determining a rate of change in urea concentration, and identifying a rate of peripheral perfusion and changes in the rate of peripheral perfusion from the rate of change in urea concentration in real-time or near real-time.

Example 2 relates to the method of Example 1, wherein the concentration of urea is measured in real time or near-real time.

Example 3 relates to the method of any of Examples 1-2, wherein the concentration of urea is measured via a near-infrared spectroscopic sensor or electrochemical biosensor.

Example 4 relates to the method of any of Examples 1-3, wherein the concentration of urea is measured on a dialysate effluent line.

Example 5 relates to the method of any of Examples 1-4, wherein the concentration of urea is measured on a dialysis machine after a dialyzer.

Example 6 relates to the method of any of Examples 1-5, further comprising storing urea concentration data for a patient over multiple dialysis treatments generating a urea concentration profile.

Example 7 relates to the method of any of Examples 1-6, further comprising alerting a user to a change in the rate of peripheral perfusion that is indicative of an adverse hemodynamic event.

Example 8 relates to the method of any of Examples 1-7, further comprising determining a dialysis dosage actually given.

Example 9 relates to the method of any of Examples 1-8, further comprising measuring the concentration of urea before and after a dialyzer to measure urea clearance by a dialyzer membrane.

In Example 10, a system for monitoring dialysis, comprising a dialysis machine, a urea monitoring sensor disposed on the dialysis machine, the urea monitoring sensor configured to measure a concentration of urea over time, and a processor in communication with the urea monitoring sensor, wherein the processor determines a rate of change in the concentration of urea over time, and wherein the processor determines a rate of peripheral perfusion.

Example 11 relates to the system of Example 10, wherein the urea monitoring sensor is a non-destructive near infrared spectroscopic sensor or an electrochemical biosensor.

Example 12 relates to the system of any of Examples 10-11, wherein the urea monitoring sensor is in communication with a dialysate effluent line of the dialysis machine.

Example 13 relates to the system of any of Examples 10-13, wherein the urea monitoring sensor is located adjacent to a dialyzer of the dialysis machine.

Example 14 relates to the system of any of Examples 10-14, further comprising an ultrafiltration port and wherein the urea monitoring sensor is configured to measure urea concentration in a blood ultrafiltrate from the ultrafiltration port.

Example 15 relates to the system of any of Examples 10-15, wherein the rate of peripheral perfusion can be determined from the equation:

$$U(t) = U_0 \exp\left(-\frac{Kt}{V_{eff}(t)}\right),$$

where U is a concentration of urea, where K is a dialyzer clearance value, where t is a time from start of dialysis, and where $V_{eff}(t)$ is an effective patient volume being cleared of urea at a given time.

Example 16 relates to the system of any of Examples 10-15, wherein $V_{eff}(t)$ is determined from the equation:

$$V_{eff}(t) = -\frac{K}{\frac{d[\ln(U)]}{dt}}.$$

Example 17 relates to the system of any of Examples 10-16, wherein rates of change of in the concentration of urea in the core and peripheral blood volumes is given by:

$$\frac{dU_c}{dt} = -\frac{K}{V_c}U_c + Q_p(U_p - U_c) \text{ and } \frac{dU_p}{dt} = -\frac{Q_p(U_p - U_c)}{V_p},$$

where $U_c$ is urea concentration of the core compartment, $V_c$ is the volume of the core compartment and $U_p$ is urea concentration of the peripheral compartment, and $V_p$ is the volume of the peripheral compartment, where K is a dialyzer clearance value, where t is a time from start of dialysis, and where $Q_p$ is the rate of peripheral blood perfusion.

Example 18 relates to the system of any of Examples 10-17, wherein the rate of peripheral perfusion is adjusted to account for one or more of urea generation during dialysis, residual kidney clearance, ultrafiltration, interruptions to dialysis due to bypass or machine warnings, and changes in the dialysis parameters.

Example 19 relates to the system of any of Examples 10-18, wherein the processor is configured to detect inadequate perfusion or changes in peripheral perfusion that signal onset of hemodynamic instability and/or impending hypotensive events.

In Example 20, a method of measuring peripheral perfusion during hemodialysis comprising: measuring urea concentration in used dialysate; generating a urea concentration profile; determining a rate of change in urea concentration over time; and determining a rate of peripheral perfusion from the following equation:

$$U(t) = U_0 \exp\left(-\frac{Kt}{V_{eff}(t)}\right),$$

where U is a concentration of urea, where K is a dialyzer clearance value, where t is a time from start of dialysis, and $V_{eff}(t)$ is an effective patient volume being cleared of urea at a given time.

Various implementations comprise the necessary components required to effectuate the described processes. For example, certain implementations feature a system of one or more computers configured to perform particular operations or actions by virtue of having software, firmware, hardware, or a combination of them installed on the system that in operation causes or cause the system to perform the actions. It is understood that one or more computer programs can be configured to perform particular operations or actions by virtue of including instructions that, when executed by data processing apparatus, cause the apparatus to perform the actions. Other implementations include corresponding computer systems, apparatus, and computer programs recorded on one or more computer storage devices, each configured to perform the actions of the methods.

While multiple embodiments are disclosed, still other embodiments of the disclosure will become apparent to those skilled in the art from the following detailed description, which shows and describes illustrative embodiments of the invention. As will be realized, the disclosure is capable of modifications in various obvious aspects, all without departing from the spirit and scope of the disclosure. Accordingly, the drawings and detailed description are to be regarded as illustrative in nature and not restrictive.

BRIEF DESCRIPTION OF THE DRAWINGS

FIG. 2C is a graph of urea concentration and peripheral perfusion of a clinical patient over time during a dialysis treatment, according to one example.

FIG. 2D is a graph of urea concentration and peripheral perfusion of a clinical patient over time during a dialysis treatment, according to one example.

DETAILED DESCRIPTION

Figure 1A:
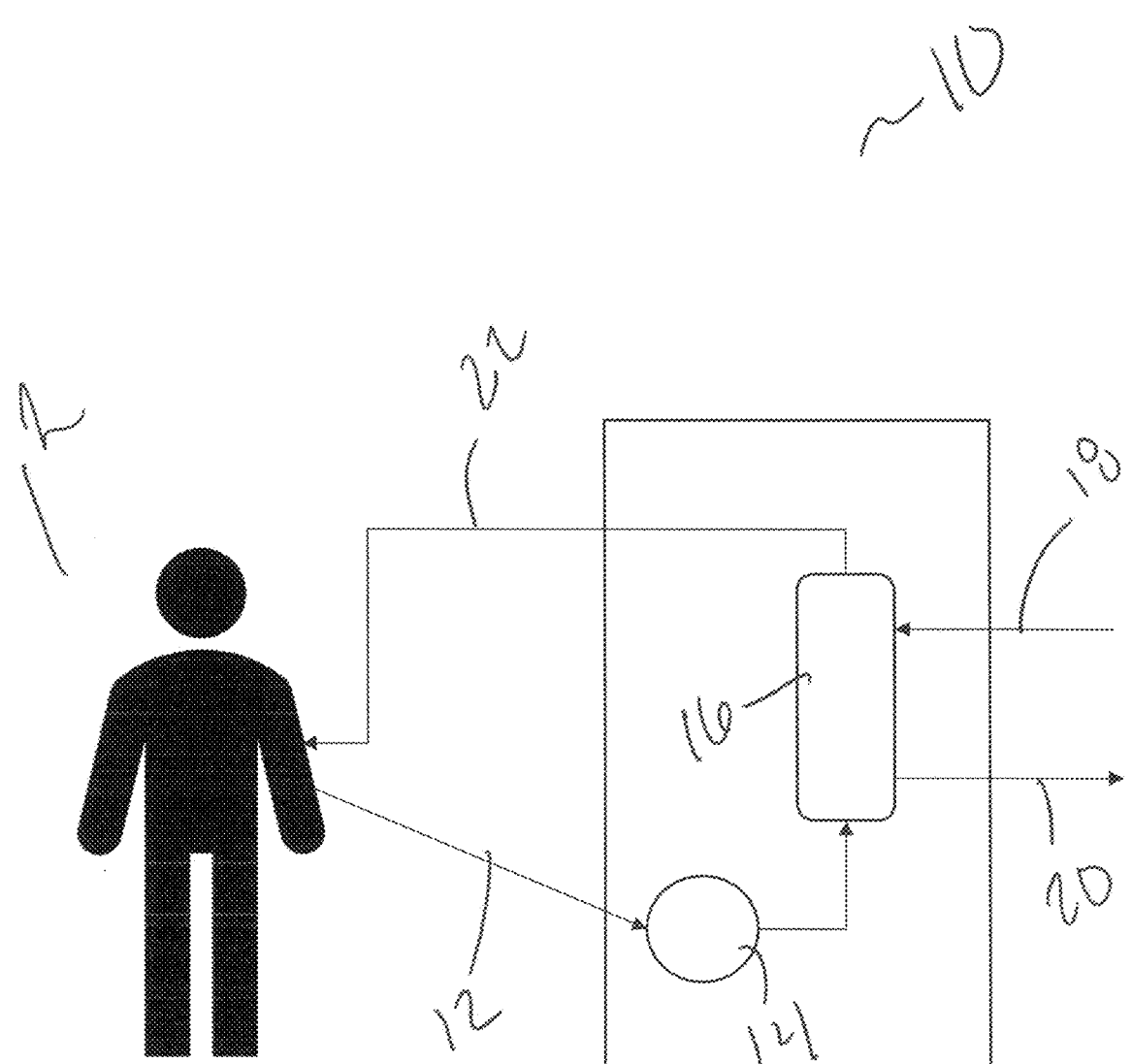
FIG. 1A is a schematic diagram of dialysis, according to one implementation.

Disclosed herein are methods and related systems and devices for measuring and analyzing physiological information during dialysis treatment. In various implementations, the method includes analyzing the concentration of urea over time in blood entering the dialyzer and/or in the effluent dialysate line. In these implementations, the time-dependence of the concentration of urea is determined by various dialysis parameters and by the rate of perfusion of a patient's peripheral tissues. Further described herein are methods for determining the extent of perfusion, trends in the rate of perfusion, and fluctuation in the rate of perfusion in real time or near real-time while a patient is undergoing a dialysis treatment.

Various implementations allow for improved methods for dialysis dose quantification and garnering physiological information that can improve dialysis efficiency. Further, certain implementations provide tools that nephrologists and other stakeholders can use to detect and mitigate adverse hemodynamic instabilities. These systems and methods can be applied during each dialysis session and corrections can be made before the end of the dialysis session.

The extent of perfusion, trends in the rate of perfusion, and fluctuations in the rate of perfusion are critical physiologic parameters for nephrologists and other stakeholders to follow in the treatment and management of patients on dialysis. As will be understood by this disclosure, the measurement and quantitative analysis of perfusion parameters during dialysis may allow for reducing and/or eliminating adverse clinical events during dialysis treatments.

Various implementations allow for measurement of peripheral perfusion rates in real-time or near real-time. Further implementations relate to the early identification of adverse hemodynamics and the prevention of adverse clinical outcomes. Still further, implementations provide analytical performance, such as providing temporal resolution, signal-to-noise ratio, and/or instrumental stability over time, to enable detection of changes in peripheral perfusion rates, as described herein.

The term "patient" includes human and veterinary subjects. In some aspects of the disclosed methods, the subject and/or patient has been diagnosed with a need for a dialysis treatment.

As used herein the term "dialysis" is inclusive of any form of dialysis including hemodialysis. Further the term dialysis includes treatments conducted in at-home, outpatient, intensive care unit (ICU), and other environments.

As used herein the term "peripheral tissues" means those tissues not a part of a patient's central core blood volume and central organs, which are highly perfused.

As used herein the term "peripheral perfusion" refers to the exchange of blood from peripheral tissues to the core blood volume, that is directly impacted during the dialysis process.

As used herein the term "core blood" is the patient's blood that resides within the central organs and, thereby, is the blood that rapidly circulates through the dialysis hardware and is directly treated by the dialysis process to remove blood toxins.

Figure 1B:
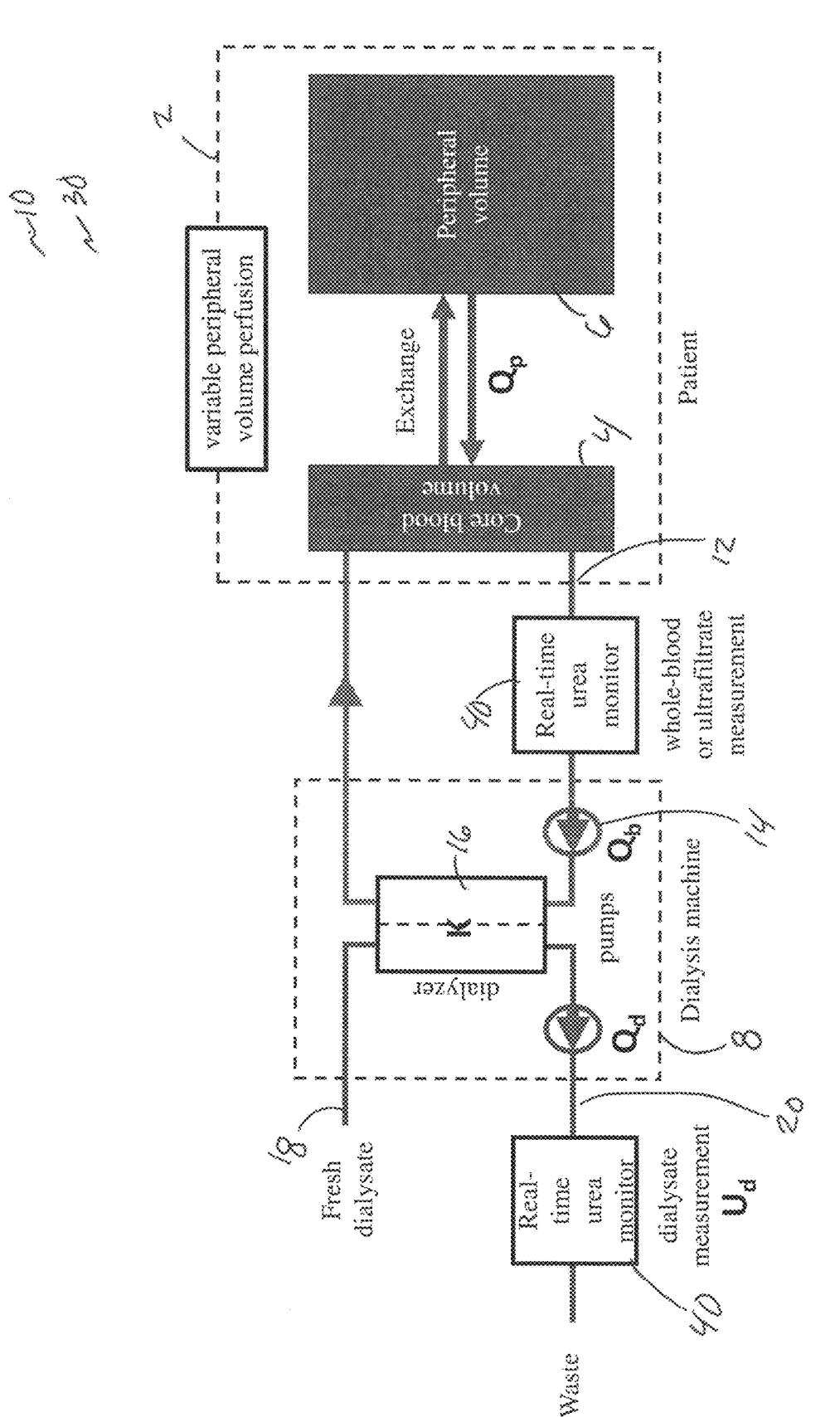
FIG. 1B is a schematic diagram of dialysis showing a two-pool model, according to one implementation.

Turning now to the figures in more detail, blood of a patient 2, when in the body, can be categorized into core blood volume 4 and peripheral blood volume 6, as shown in FIGS. 1A-1B. The rate of exchange of blood between the core blood volume 4 and peripheral blood volume 6 is termed the peripheral perfusion rate, which can vary within and between dialysis treatments.

The mechanism of dialysis treatment is well understood in the art. FIGS. 1A and 1B show exemplary diagrams of dialysis 10. During a hemodialysis treatment, core blood is removed 12 from a patient 2. The blood is then pumped 14 to a dialysis machine 8, where the blood is dialyzed/ultra-filtered 16. Fresh dialysate is added 18 during the treatment, and the used dialysate is removed 20 from the dialyzer along with metabolic waste, including urea. This used dialysate is often referred to as "effluent". The filtered blood can then be returned 22 to the patient 2, as would be understood.

It is known in the art that non-continuous dialysis (e.g., on a three (3) treatments per week schedule) creates disequilibrium in the body. In a "single-compartment" or "single-pool" model of urea removal, the patient's fluid volume is considered to be a single well-mixed "pool". In that case, the urea concentration in the patient should decrease exponentially, as reflected in Eq. 1, below:

$$U(t) = U_0 \exp\left(-\frac{Kt}{V}\right),$$ [Eq. 1]

where U is the uniform concentration of urea in the patient's blood volume, K is the clearance of the dialyzer, t is the time from the start of dialysis, and V is the patient's urea distribution volume. However, this model is not adequate to describe the urea concentration dynamics observed during clinical dialysis because it fails to account for the dynamics of disequilibrium. In particular, Equation 1 fails to explain the rapid initial drop of urea and the rebound in urea concentration at the end of dialysis.

The rapid initial drop in urea concentration at the dialyzer and the rebound at the end of dialysis can be explained using the "two-pool" model of urea kinetics. According to the two-pool model, the body is conceptually divided into two compartments: one that includes the core blood volume and highly perfused organs, where the blood is assumed to be well mixed, and a peripheral volume that has a limited rate of exchange with the core blood volume. That rate of exchange is referred to as the peripheral perfusion rate.

The peripheral compartment consists of tissues such as the skin and skeletal muscles, which contain a large percentage of the body's water volume, but which receive only a part of the cardiac output—blood. During dialysis, urea is cleared from the core blood volume. Urea in the peripheral compartment is cleared only as the peripheral volume is perfused with blood from the core volume. Because of the finite rate of perfusion, this peripheral volume does not stay in equilibrium with the core blood volume during dialysis.

The rate of perfusion of the peripheral space may vary in response to several factors. For example, during exercise, overall cardiac output increases substantially, and a greater fraction of cardiac output is directed to skeletal muscles, increasing the rate of peripheral perfusion. In another example, when the body is cold, blood flow to the skin is reduced in order to maintain core body temperature, decreasing the rate of peripheral perfusion. In a still further example, the body's response to low blood pressure is to increase the heart rate in order to compensate for decreased cardiac filling and to decrease blood flow to the peripheral tissues in order to maintain perfusion of the core organs, thereby decreasing the rate of peripheral perfusion. Additionally, it is understood that peripheral perfusion typically decreases with age and can be impaired by other factors such as peripheral vascular disease.

Non-continuous forms of dialysis inherently push the body out of equilibrium in order to remove in 3-4 hours the uremic toxins and excess water that have built up over the previous 2-3 days. The extent of disequilibrium is proportional to the rate of dialysis and fluid removal.

There are several complications/side effects associated with dialysis, including, but not limited to, cramps, nausea and vomiting, headache, chest pain, itching, and disequilibrium syndrome as would be appreciated by those of skill in the art. The most common and most serious complication, however, is hypotension. It is understood that hypotensive events can be triggered by overly aggressive fluid removal. As noted above, and as shown in FIGS. 1A-1B, fluid is removed directly from the blood volume by ultrafiltration across the dialyzer. Under normal circumstances, fluid that is removed from the blood volume is replenished by the movement of fluid from body tissues into the blood. However, if fluid is removed faster than it can be replenished, the blood volume will decrease, resulting in hypovolemia.

The body's natural response to hypovolemia involves increasing the heart rate and constriction of the arterioles and vascular bed. This response can reduce perfusion of peripheral tissues and limit the refilling of the blood volume by fluid in the peripheral tissues. Thus, there is a positive feedback dynamic that can reinforce hypovolemia if the rate of ultrafiltration is not reduced. If unchecked, sustained vascular tension can lead to a vasovagal relaxation and an acute hypotensive event. This type of "crash" can be very dangerous to the patient and cause ischemia in critical organs.

Each patient's ability to tolerate disequilibrium is different. These natural responses work best in healthy patients. It is understood that seriously ill and/or older patients may have reduced ability to sustain peripheral perfusion. Further, certain factors, such as diabetes and vascular disease, are understood to impair recovery from disequilibrium.

Discussed herein are various methods, devices, and systems that allow for estimation of the rate of peripheral perfusion from the dynamics of urea removal. As will be understood in light of this disclosure the ability to measure peripheral perfusion may allow for the ability to detect hemodynamic instability and provide warnings of acute hypotensive events.

In one exemplary implementation, the rate of peripheral perfusion can be determined using Eq. 1 and substituting the patient's urea distribution volume (V) with an effective volume that represents the patient volume being cleared of urea at any given time ($V_{eff}(t)$). In this implementation, the expression Kt/V is changed from a measure of prescribed or delivered dose into an expression that describes the logarithmic change in the urea concentration with time.

In some implementations, if the dialyzer clearance, K, is known, such as from tables provided by the manufacturer or from ionic dialysance measurements. Other sources of dialyzer clearance values, K, are possible and would be recognized by those of skill in the art. In these implementations, the effective volume ($V_{eff}(t)$) can be calculated from:

$$V_{eff}(t) = -\frac{K}{\frac{d[\ln(U)]}{dt}} \qquad \text{[Eq. 2]}$$

When the natural log of the urea concentration drops rapidly, $V_{eff}$ will be small. A large $V_{eff}$ implies a slower decrease in the natural log of the urea concentration. At the start of a normal dialysis session, when dialysis is primarily clearing the core blood volume, $V_{eff}$ will correspond to the core blood volume and be much less than the patient's urea distribution volume. As the dialysis treatment progresses, $V_{eff}$ will typically approach the patient's urea distribution volume.

In one example, if it is observed that $V_{eff}$ remains substantially below the urea distribution volume, the patient's peripheral perfusion may be impaired.

In another example, if substantial fluctuations in $V_{eff}$ are observed this may indicate hemodynamic instability and an impending hypotensive event. In this example, early intervention may be possible to preempt or proactively treat such an event.

In another implementation, a two-pool model of urea kinetics, shown in FIG. 1B, may be used for a quantitative description of peripheral perfusion. Neglecting ultrafiltration, for simplicity, the concentration of urea in the effluent dialysate line, $U_d$, is related to the concentration of urea in the core blood volume ($U_c$) by:

$$U_d = \frac{K}{Q_d} U_c, \qquad \text{[Eq. 3]}$$

where K is the clearance of the dialyzer and $Q_d$ is the rate of dialysate flow through the dialyzer. Within the two-pool model, the rates of change of the urea concentration in the core and peripheral blood volumes are then given by:

$$\frac{dU_c}{dt} = -\frac{K}{V_c} U_c + Q_p(U_p - U_c) \qquad \text{[Eq. 4A]}$$

$$\frac{dU_p}{dt} = -\frac{Q_p(U_p - U_c)}{V_p} \qquad \text{[Eq. 4B]}$$

where $U_c$, $V_c$ and $U_p$, $V_p$ are the urea concentration and volume of the core and peripheral compartments, respectively, and $Q_p$ is the rate of peripheral blood perfusion. In this implementation, the sum $V_u = V_c + V_p$ is the patient's total urea distribution volume.

Given K, $V_c$ $V_p$, and initial values for $U_c = U_p$, along with a time profile for $Q_p(t)$, the differential equations in Eq. 4A and 4B can be solved to obtain the time profile of the urea concentration in the core blood volume, $U_c(t)$.

In another implementation, given measured values for $U_c(t)$, the equations (Eq. 4A and 4B) can be integrated to determine an estimate for $Q_p(t)$.

Those skilled in the art will recognize that correction terms can be added to this formulation to account for factors such as urea generation during dialysis, residual kidney clearance, ultrafiltration, interruptions to dialysis due to bypass or machine warnings, and changes in the dialysis parameters (flow rates, dialyzer clearance, etc.). In addition, more complex models for fluid movement in the body, which may include the use of additional "pools" or a distribution of urea in various compartments of the body may be used. $Q_p(t)$ is a measure of the overall rate of perfusion of peripheral tissues in the body.

In these and other implementations, the peripheral perfusion rate can be illustrated by first assuming a functional form for $Q_p(t)$, calculating the resulting time profile for $U_c(t)$, and then calculating the concentration of urea in the effluent dialysate line, $U_d(t)$ (Eq. 3). A stakeholder or processor can then simulate the result of measurements of urea concentration in the effluent dialysate by sampling the above $U_d(t)$ profile at regular intervals and numerically adding simulated measurement noise.

Figure 2A:
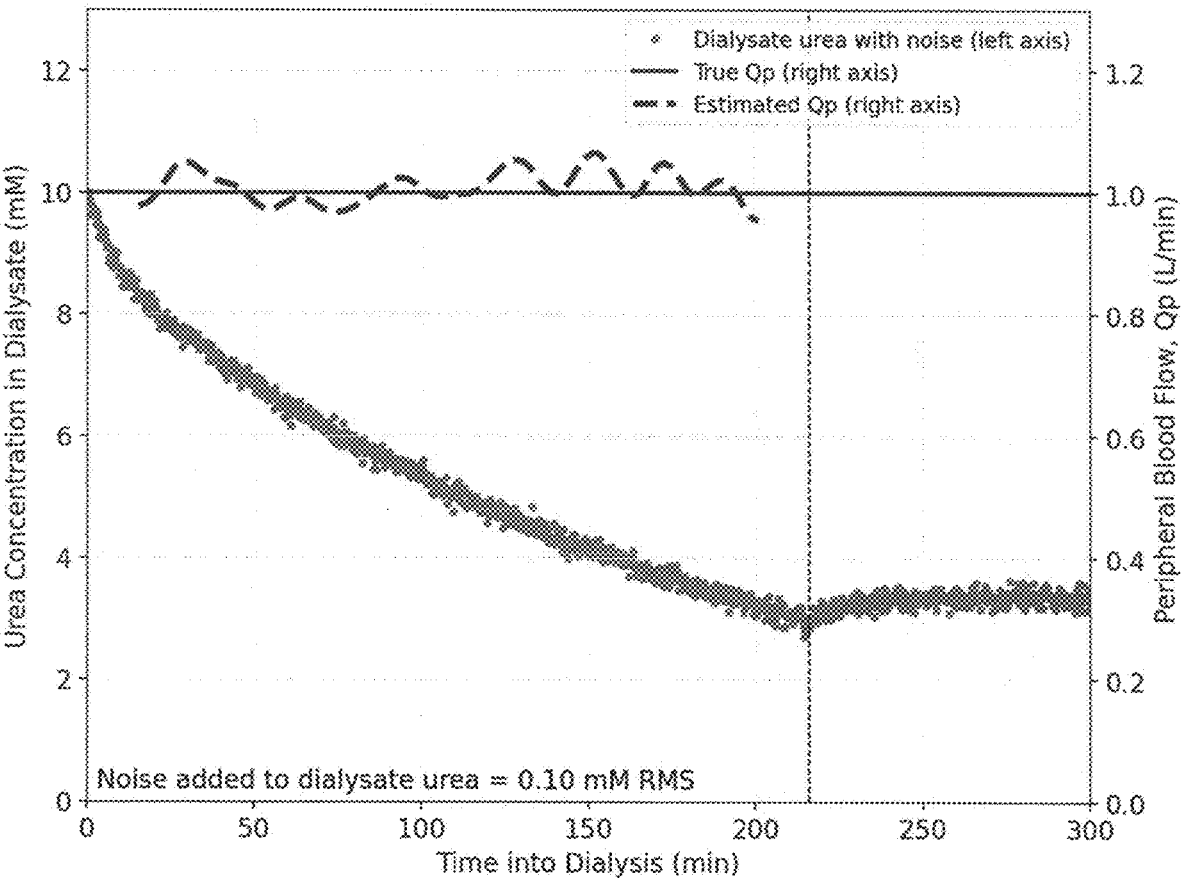
FIG. 2A is a graph of urea concentration over time during a dialysis treatment, according to one example.
Figure 2B:
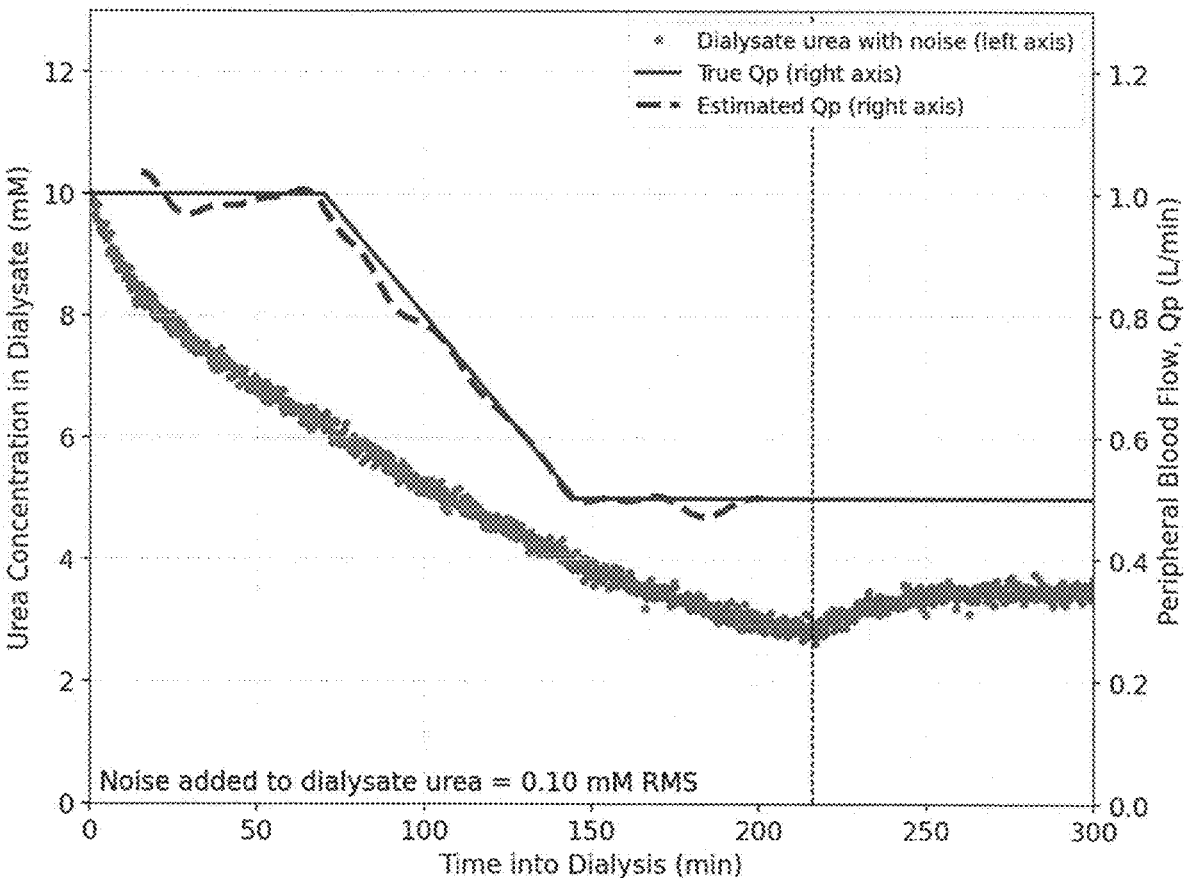
FIG. 2B is a graph of urea concentration over time during a dialysis treatment, according to one example.

In these implementations, from the noisy sampled values of $U_d(t)$, the original function, $Q_p(t)$ can be estimated. This process is illustrated in FIGS. 2A-D. In FIG. 2A the functional form of $Q_p(t)$ is assumed to be a constant 0.7 L/min or, as shown in the implementation of FIG. 2B, $Q_p(t)$ is a function that starts at 1 L/min and drops to 0.5 L/min over the course of 50 minutes. In this example, simulated measurements of $U_d(t)$ with 0.1 mM of added noise are re-integrated to obtain an estimate of $Q_p(t)$. In both examples, the estimated $Q_p(t)$ tracks the true values. The decrease in $Q_p(t)$ in FIG. 2B is well reproduced by this method even though there is no obvious visual indication in the values for $U_d(t)$. Modeled urea concentrations in the core and peripheral volumes can be used to calculate the equilibrated blood urea concentration and a value for the equilibrated Kt/V that does not rely on general expressions that assume normal rates of perfusion.

FIGS. 2C and 2D show data from two patients in an outpatient dialysis clinic. As can be seen, the data from actual patients are similar to the simulated data of FIGS. 2A-B. In FIG. 2C, the perfusion rate is calculated to be 1 L/min until 08:30, after which the rate decreases to 0.25 L/min by the end of the treatment. The equilibrated Kt/V for this session is 1.22. In FIG. 2D, the perfusion rate drops quickly from an initial value of 0.7 L/min to 0.5 L/min over the first 1.5 hrs of the treatment, and then falls to 0.1 L/min by 15:30. The equilibrated Kt/V for this treatment was 0.67, which is consistent with impaired peripheral perfusion. The difference in the equilibrated Kt/V (1.22 vs. 0.67) would not normally be expected given that the urea reduction ration is about 0.8 for both treatments.

The difference between the urea concentration in the core blood volume and that in the peripheral volume can be confirmed by measurement of urea concentrations in the peripheral space using techniques such as subdermal ultra-filtration or microdialysis or a needle-based or noninvasive measurement of urea concentration in tissue.

As will be appreciated in light of this disclosure, the value and trends in the estimates of the peripheral perfusion rate, $Q_p(t)$, can be used by nephrologists and other stakeholders to detect inadequate perfusion or changes in peripheral perfusion that signal the onset of hemodynamic instability and impending hypotensive events.

Figure 3:
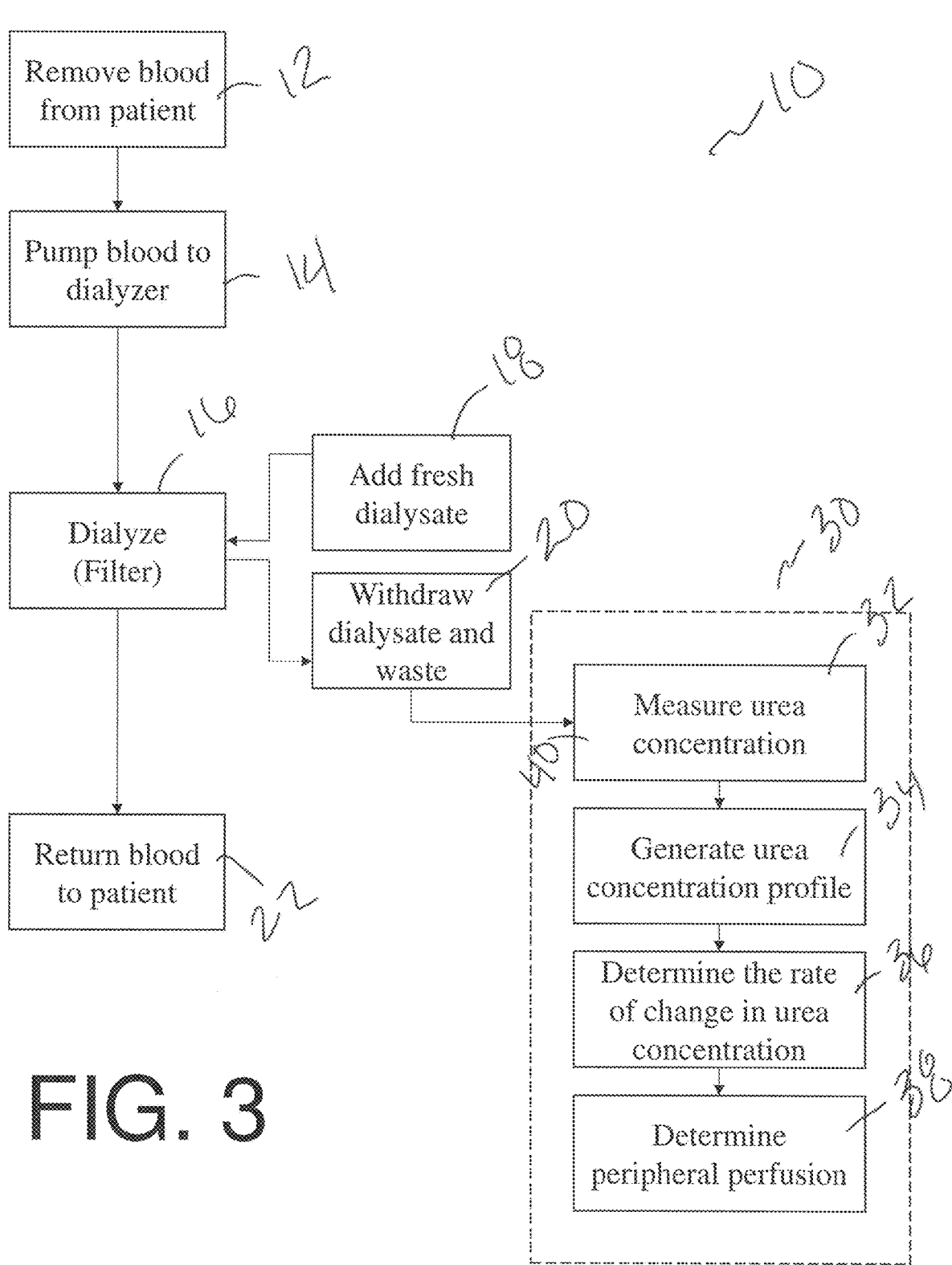
FIG. 3 is a system diagram for the dialysis and analysis system, according to one implementation.
Figure 4A:
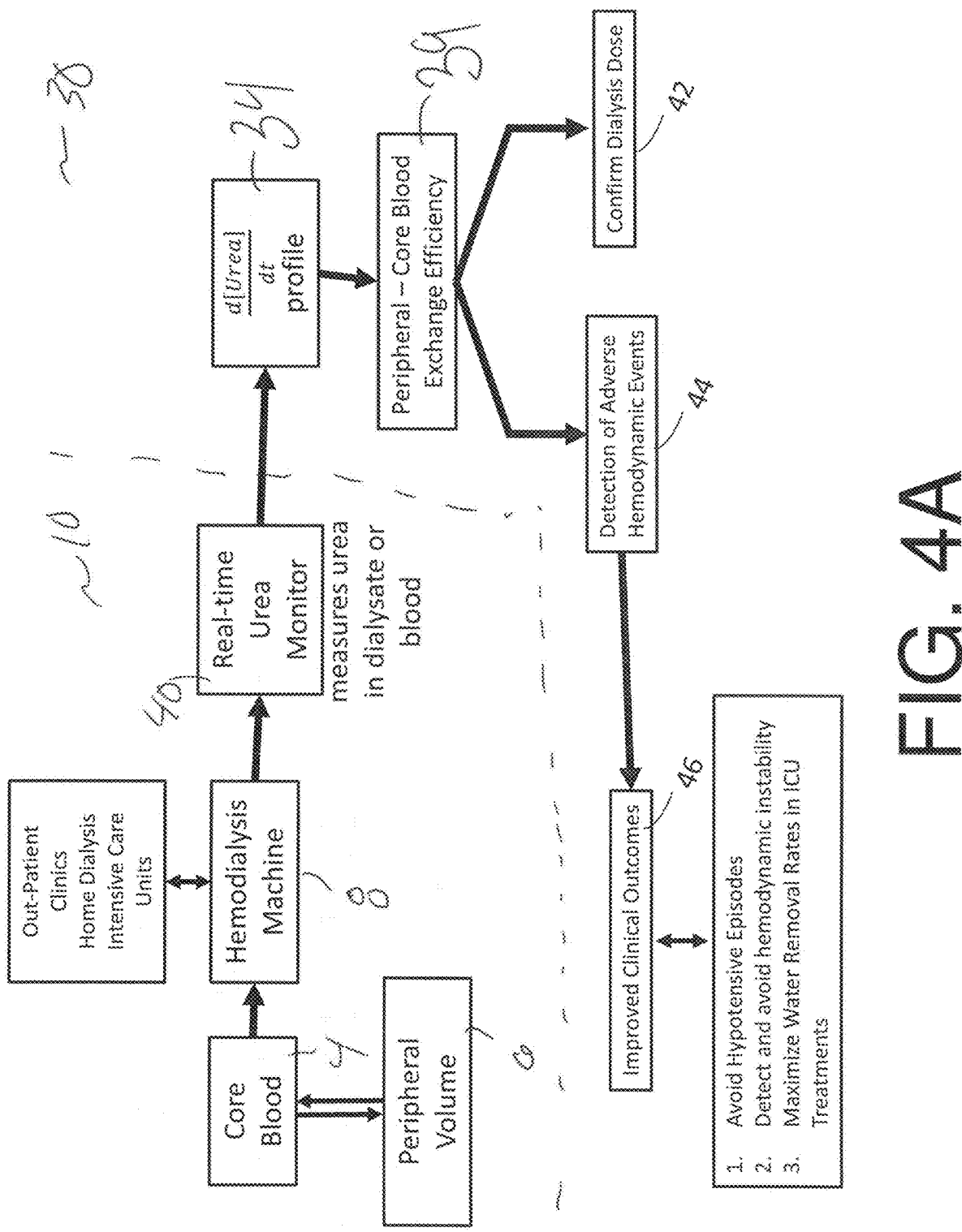
FIG. 4A is system diagram for the dialysis and analysis system, according to one implementation.

In the various implementations, described herein are devices and methods for taking continuous or periodic measurements of concentrations of urea in the removed dialysate effluent 20, such as via a real-time urea monitor 40, shown in FIGS. 1B, 3, and 4A. The analysis system 30 includes various steps that may be performed in any order or not at all. In certain implementations, the various steps are performed iteratively.

Turning now to FIG. 3, in certain implementations, the urea concentration is measured 32 using one or more real-time urea monitors 40. The real-time urea monitor 40 according to various implementations may include one or more sensors such as nondestructive near infrared spectro-scopic sensors, electrochemical biosensors and the like. Various such sensors are known and appreciated by those of skill in the art. In some implementations, a real-time urea monitor 40 is located at the dialysate effluent line. In various alternative implementations, a real-time urea monitor 40 is located at the dialysis machine 8 after the dialyzer such that the urea monitor 40 may measure urea removed from the blood during the dialysis treatment. In various implementa-tions, more than one urea monitor 40 is used, for example one monitor 40 may measure urea concentration in the blood prior to entering the dialyzer and a second urea monitor 40 may measure urea concentration in the used dialysate efflu-ent line.

In various implementations, the dialysis machine 8 may include a separate ultrafiltration port. The ultrafiltration port is constructed and arranged to permit sampling of a volume of blood ultrafiltrate prior to the dialyzer. A urea monitor 40 may be used to measure urea concentration in this blood ultrafiltrate.

In certain implementations, shown in FIG. 3, the urea concentration in the dialysis effluent or in the patient blood just after removal 12 from the body prior to entering the dialyzer is measured 32 in real-time or near real-time via the real-time urea monitor 40.

The urea concentration measurement should have a spe-cific time resolution, high signal-to-noise ratio, and opera-tional stability. High quality urea concentration measurements may be important for distinguishing subtle/small variations in the urea concentration signals.

In various implementations, the system 30 includes a further optional step of generating 34 a urea concentration profile for a patient or population of patients over time, such as during and/or over a series of dialysis treatments. The urea concentration profile may be generated 34 using the measured 32 urea concentrations over time.

In a further optional step, the system 30 determines 36 the rates of change in urea concentration from the urea concen-tration profile and/or measured 32 urea concentration.

In another optional step, the system 30 determines 38 rates of peripheral perfusion from an analysis of the rate curve defined as the measured 32 concentration of urea as a function of time, defined as: d[Urea]/dt.

As noted above, changes in the measured rates of urea concentration (d[ln(U)]/dt) are indicative of changes in peripheral perfusion rates. It would be understood that certain changes in the measured rates of urea concentration may occur due to changes in other dialysis parameters including, but not limited to, blood flow rate, dialysate flow rate, changes in K (dialyzer clearance of urea), and ultrafil-tration rates. These changes can be controlled for as changes due to these and other parameters are not indicative of changes in peripheral perfusion rates.

Further, differences in real-time peripheral perfusion rates are direct measures of physiological changes related to hemodynamic exchange between central blood and periph-eral blood. As patterns in peripheral perfusion change over time this measurement can be used to identify adverse hemodynamic events before the onset of clinical symptoms and/or confirm optimum dialysis dosage. Further the data regarding peripheral perfusion can be used for early problem detection and avoidance, such as to quantify the amount of dialysis truly given, and to tune dialysis parameters to achieve the optimized dose. In certain implementations, the rate of perfusion can be combined with other clinical mea-sures that are associated with hemodynamic instability, such as blood pressure and heart rate, for detection of adverse hemodynamic events.

Figure 4B:
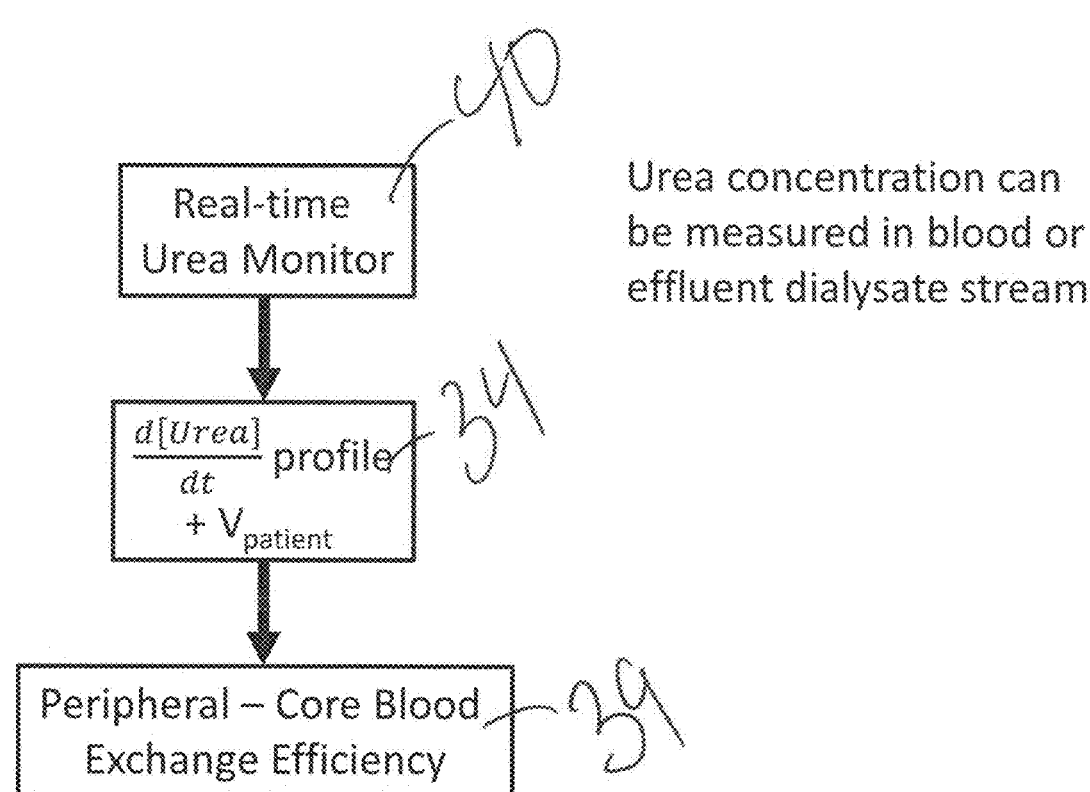
FIG. 4B is a system diagram for an analysis system, according to one implementation.

FIGS. 4A and 4B show various other implementations of dialysis 10 and the system 30. In various implementations, the system 30 determines the peripheral-core blood exchange efficiency 39 from the generated urea concentra-tion profile 34, discussed above. The exchange efficiency 39 may then be used to confirm 42 the dialysis dose and/or detect 44 adverse hemodynamic events.

In various implementations, the system 30 provides 46 for improved clinical outcomes, certain non-limiting examples including: avoidance of hypotension episodes, minimal elec-trolyte imbalance induced cramping, maximizing rates of excess water removal in ICU patients and detecting and avoiding hemodynamic instability, among others.

In various alternative implementations, including at least two urea monitors 40, measuring concentrations of urea before and after the dialyzer, the system 30 may compare the detected urea concentrations before and after the dialyzer to measure urea clearance by the dialyzer membrane (K).

Although the disclosure has been described with refer-ences to various embodiments, persons skilled in the art will recognized that changes may be made in form and detail without departing from the spirit and scope of this disclo-sure.

What is claimed is:

1. A method of conducting dialysis, comprising:
   measuring a concentration of urea in a dialysis effluent over time;

determining a rate of change in urea concentration;

identifying a rate of peripheral perfusion and changes in the rate of peripheral perfusion from the rate of change in urea concentration in real-time or near real-time using a multi-compartment model, and operating a dialysis machine based on the identified rate of peripheral perfusion and changes in the rate of peripheral perfusion, wherein the rate of peripheral perfusion is determined from the following equations:

$$\frac{dU_c}{dt} = -\frac{K}{V_c} U_c + Q_p(U_p - U_c) \text{ and } \frac{dU_p}{dt} = -\frac{Q_p(U_p - U_c)}{V_p};$$

wherein $U_p$ is a peripheral concentration,
wherein $U_c$ is a core concentration,
wherein $Q_p$ is the rate of peripheral perfusion,
wherein $V_p$ is a peripheral volume
wherein $V_c$ is a core volume, and
wherein K is a dialyzer clearance value.

2. The method of claim 1, wherein the concentration of urea is measured in real time or near-real time.

3. The method of any of claim 1, wherein the concentration of urea is measured via a near-infrared spectroscopic sensor or electrochemical biosensor.

4. The method of any of claim 1, wherein the concentration of urea is measured on a dialysate effluent line.

5. The method of any of claim 1, wherein the concentration of urea is measured on a dialysis machine after a dialyzer.

6. The method of any of claim 1, further comprising storing urea concentration data for a patient over multiple dialysis treatments generating a urea concentration profile.

7. The method of any of claim 1, further comprising alerting a user to a change in the rate of peripheral perfusion that is indicative of an adverse hemodynamic event.

8. The method of any of claim 1, further comprising determining a dialysis dosage actually given.

9. The method of any of claim 1, further comprising measuring the concentration of urea before and after a dialyzer to measure urea clearance by a dialyzer membrane.

10. A system for monitoring dialysis, comprising:
(a) a dialysis machine;
(b) a urea monitoring sensor disposed on the dialysis machine, the urea monitoring sensor configured to measure a concentration of urea over time; and
(c) a processor in communication with the urea monitoring sensor, wherein the processor determines a rate of change in the concentration of urea over time using a multi-compartment model, and wherein the processor determines a rate of peripheral perfusion;
wherein the dialysis machine is configured to control dialysis parameters based on a determination of the rate of peripheral perfusion;
wherein the rate of peripheral perfusion is determined from the following equations:

$$\frac{dU_c}{dt} = -\frac{K}{V_c} U_c + Q_p(U_p - U_c)$$

-continued
and $$\frac{dU_p}{dt} = -\frac{Q_p(U_p - U_c)}{V_p};$$

wherein $U_p$ is a peripheral concentration,
wherein $U_c$ is a core concentration,
wherein $Q_p$ is the rate of peripheral perfusion,
wherein $V_p$ is a peripheral volume
wherein $V_c$ is a core volume, and
wherein K is a dialyzer clearance value.

11. The system of claim 10, wherein the urea monitoring sensor is a non-destructive near infrared spectroscopic sensor or an electrochemical biosensor.

12. The system of any of claim 10, wherein the urea monitoring sensor is in communication with a dialysate effluent line of the dialysis machine.

13. The system of any of claim 10, wherein the urea monitoring sensor is located adjacent to a dialyzer of the dialysis machine.

14. The system of any of claim 10, further comprising an ultrafiltration port and wherein the urea monitoring sensor is configured to measure urea concentration in a blood ultrafiltrate from the ultrafiltration port.

15. The system of any of claim 10, wherein the calculation of the rate of peripheral perfusion is adjusted to account for one or more of urea generation during dialysis, residual kidney clearance, ultrafiltration, interruptions to dialysis due to bypass or machine warnings, and changes in the dialysis parameters.

16. The system of any of claim 10, wherein the processor is configured to detect inadequate perfusion or changes in peripheral perfusion that signal the onset of hemodynamic instability and/or impending hypotensive events.

17. A method of conducting hemodialysis measuring peripheral perfusion during hemodialysis comprising:
measuring urea concentration in used dialysate;
generating a urea concentration profile;
determining a rate of change in urea concentration over time; and
determining a rate of peripheral perfusion from the following equations:

$$\frac{dU_c}{dt} = -\frac{K}{V_c} U_c + Q_p(U_p - U_c)$$

and $$\frac{dU_p}{dt} = -\frac{Q_p(U_p - U_c)}{V_p};$$

wherein $U_p$ is a peripheral concentration,
wherein $U_c$ is a core concentration,
wherein $Q_p$ is the rate of peripheral perfusion,
wherein $V_p$ is a peripheral volume,
wherein $V_c$ is a core volume, and
wherein K is a dialyzer clearance value; and
operating a dialysis machine based on the identified rate of peripheral perfusion and changes in the rate of peripheral perfusion.

* * * * *